United States Patent
Kanowitz

(10) Patent No.: US 10,722,671 B2
(45) Date of Patent: Jul. 28, 2020

(54) METHOD AND APPARATUS FOR DETERMINING OPTIMAL ENDOTRACHEAL TUBE SIZE

(71) Applicant: Securisyn Medical, LLC, Highlands Ranch, CO (US)

(72) Inventor: Arthur Kanowitz, Littleton, CO (US)

(73) Assignee: Securisyn Medical, LLC, Highlands Ranch, CO (US)

( * ) Notice: Subject to any disclaimer, the term of this patent is extended or adjusted under 35 U.S.C. 154(b) by 750 days.

(21) Appl. No.: 14/712,724

(22) Filed: May 14, 2015

(65) Prior Publication Data
US 2016/0022943 A1 Jan. 28, 2016

Related U.S. Application Data

(60) Provisional application No. 62/000,182, filed on May 19, 2014.

(51) Int. Cl.
*A61M 16/04* (2006.01)
*A61B 8/12* (2006.01)
(Continued)

(52) U.S. Cl.
CPC ..... *A61M 16/0488* (2013.01); *A61B 1/00165* (2013.01); *A61B 1/267* (2013.01);
(Continued)

(58) Field of Classification Search
CPC .......... A61M 16/0488; A61M 16/0434; A61M 2205/583; A61M 16/04; A61M 16/0402;
(Continued)

(56) References Cited

U.S. PATENT DOCUMENTS 4,449,522 A * 5/1984 Baum .................. A61M 16/04
128/200.26
5,183,031 A * 2/1993 Rossoff ................. A61B 1/267
600/120
(Continued)

OTHER PUBLICATIONS

J.-Y. Bae, H.-J. Byon, S.-S. Han, H. -S. Kim, and J. -T. Kim, "Usefulness of ultrasound for selecting a correctly sized uncuffed tracheal tube for paediatric patients", Anaesthesia Journal of the Association of Anaesthetists of Great Britain and Ireland, 2011, pp. 994-998.*

(Continued)

*Primary Examiner* — Tu A Vo
(74) *Attorney, Agent, or Firm* — Glenn H. Lenzen; Dietze and Davis, P.C.

(57) ABSTRACT

A method and apparatus for determining the optimal endotracheal tube size for the intubation of a patient based upon both optimal tube length and optimal tube diameter which are determined by using either direct or indirect measurement devices or techniques to measure the patient's glottis aperture and tracheal length. The apparatus may include a maneuverable arm, a fiber optic video guidance system and an introducer guide to maneuver an end of the apparatus around obstructions in a patient who has a difficult airway to facilitate insertion of either an optimally sized endotracheal tube or a standard endotracheal tube into the patient's airway.

6 Claims, 14 Drawing Sheets

(51) Int. Cl.
  *A61B 5/107* (2006.01)
  *A61B 1/267* (2006.01)
  *A61B 5/00* (2006.01)
  *A61B 5/0205* (2006.01)
  *A61B 5/08* (2006.01)
  *A61B 1/00* (2006.01)

(52) U.S. Cl.
  CPC .......... *A61B 5/0084* (2013.01); *A61B 5/0205* (2013.01); *A61B 5/08* (2013.01); *A61B 5/1076* (2013.01); *A61B 5/6867* (2013.01); *A61B 8/12* (2013.01); *A61M 16/0434* (2013.01); *A61M 2205/583* (2013.01)

(58) Field of Classification Search
  CPC .......... A61M 16/0404; A61M 16/0406; A61M 16/0411; A61M 26/0418; A61M 16/0425; A61M 16/042; A61M 16/0427; A61M 16/0431; A61M 16/0463; A61M 16/0475; A61B 1/00165; A61B 1/267; A61B 5/08; A61B 8/12; A61B 5/0205; A61B 5/1076; A61B 5/6867; A61B 5/0084
  See application file for complete search history.

(56) References Cited

U.S. PATENT DOCUMENTS

| | | | | |
|---|---|---|---|---|
| 5,498,231 A * | 3/1996 | Franicevic | ............. | A61B 1/267 128/200.26 |
| 6,110,200 A * | 8/2000 | Hinnenkamp | ........ | A61F 2/2496 33/512 |
| 6,146,402 A * | 11/2000 | Munoz | ................ | A61B 1/0607 606/194 |
| 6,213,937 B1 * | 4/2001 | Vivenzio | ................ | A61B 1/267 600/193 |
| 6,257,236 B1 * | 7/2001 | Dutkiewicz | ....... | A61M 16/0429 128/207.14 |
| 9,050,049 B2 * | 6/2015 | Ryan | ................... | A61B 5/1076 |
| 9,814,853 B2 | 11/2017 | Kanowitz | | |
| 2006/0064039 A1 * | 3/2006 | Griego | ................. | A61B 5/1076 600/587 |
| 2006/0155217 A1 * | 7/2006 | DeVore | ................ | A61B 5/1076 600/587 |
| 2007/0175482 A1 * | 8/2007 | Kimmel | ................ | A61B 1/018 128/207.14 |
| 2007/0203396 A1 * | 8/2007 | McCutcheon | ..... | A61B 1/00082 600/173 |
| 2008/0229597 A1 * | 9/2008 | Malandain | ........... | A61B 1/3135 33/512 |
| 2009/0090357 A1 * | 4/2009 | Schwartz | .......... | A61M 16/0488 128/200.26 |
| 2009/0143645 A1 * | 6/2009 | Matthes | ................ | A61B 1/0014 600/120 |
| 2009/0320836 A1 * | 12/2009 | Baker, Jr. | ............... | A61M 16/12 128/203.14 |
| 2010/0095969 A1 * | 4/2010 | Schwartz | .......... | A61B 1/00048 128/207.14 |
| 2010/0256476 A1 * | 10/2010 | Wood | .................... | A61M 16/04 600/409 |
| 2010/0261995 A1 * | 10/2010 | McKenna | ................ | A61B 5/06 600/424 |
| 2010/0280362 A1 * | 11/2010 | Li | ......................... | A61M 16/04 600/424 |
| 2011/0065982 A1 * | 3/2011 | Wibowo | .............. | A61B 1/2676 600/101 |
| 2011/0077466 A1 * | 3/2011 | Rosenthal | .............. | A61B 1/042 600/188 |
| 2011/0092773 A1 * | 4/2011 | Goldstein | ............. | A61B 1/015 600/187 |
| 2011/0263935 A1 * | 10/2011 | Qiu | .................... | A61B 1/00009 600/109 |
| 2012/0197086 A1 * | 8/2012 | Morris | ............... | A61B 1/00009 600/188 |
| 2012/0259173 A1 * | 10/2012 | Waldron | ............ | A61B 1/00073 600/109 |
| 2013/0109918 A1 * | 5/2013 | Pagan | ............... | A61M 16/0488 600/109 |
| 2013/0245372 A1 * | 9/2013 | Lo | ......................... | A61B 1/267 600/109 |
| 2014/0128681 A1 * | 5/2014 | Fordinal | ............... | A61B 1/267 600/194 |

OTHER PUBLICATIONS

Kumkum Gupta, Prashant Gupta, Bhwana Rastogi, Atul Krishan, Manish Jain, and Gouri Garg, "Assessment of the subglottic region by ultrasonography for estimation of appropriate size endotracheal tube: A clinical prospective study", Jul.-Dec. 2012; 6(2): 157-160.*
Chen-Hwan Cherng, Chih-Shung Wong, Che-Hao Hsu, Shung-Tai Ho, "Airway Length in Adults: Estimation of the Optimal Endotracheal Tube Length for Orotracheal Intubation", Jun. 2002.*

* cited by examiner

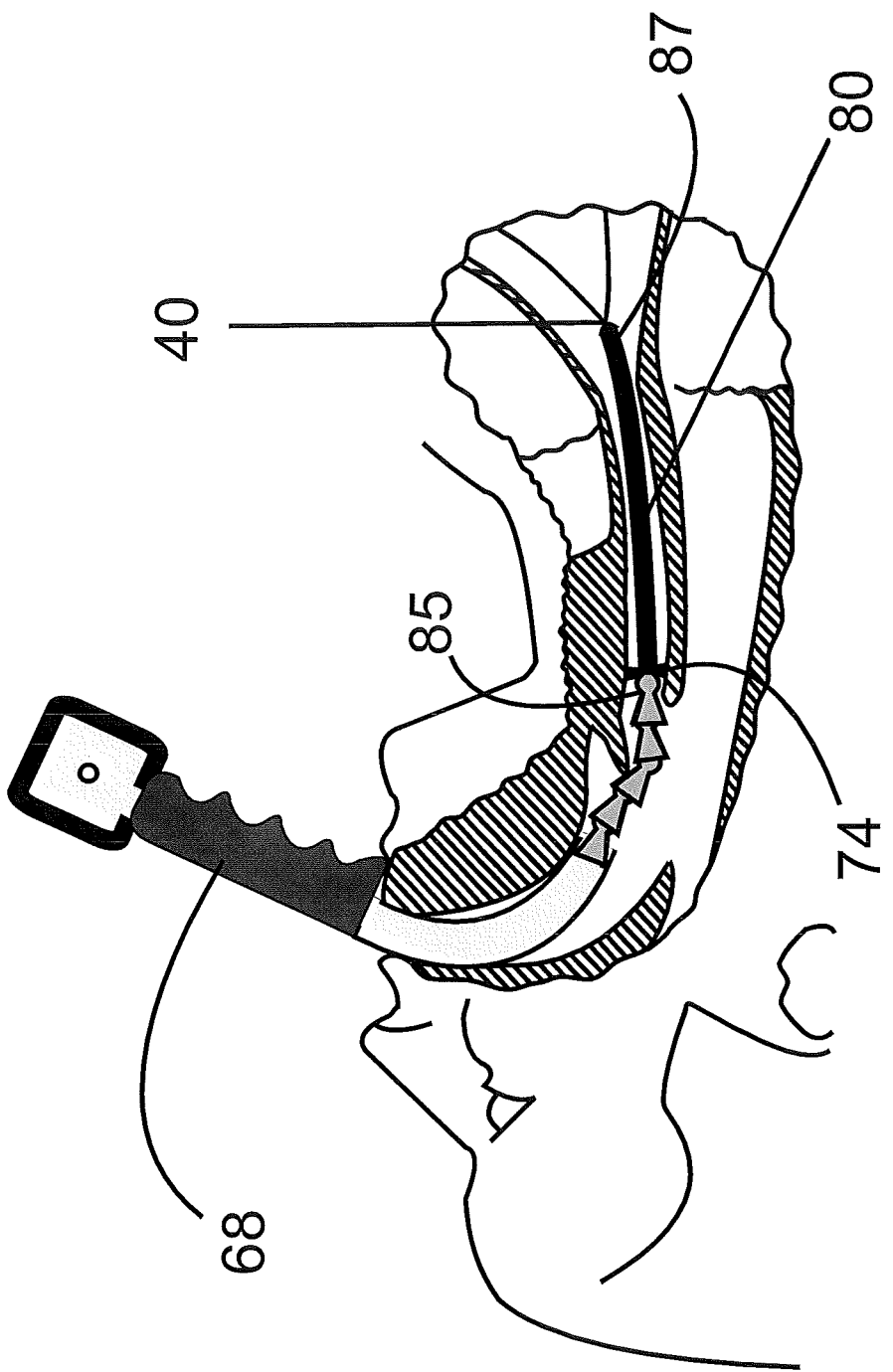

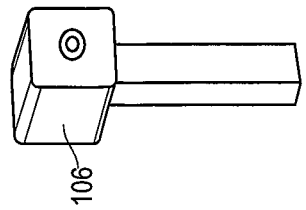
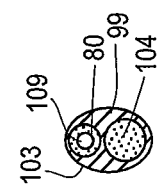
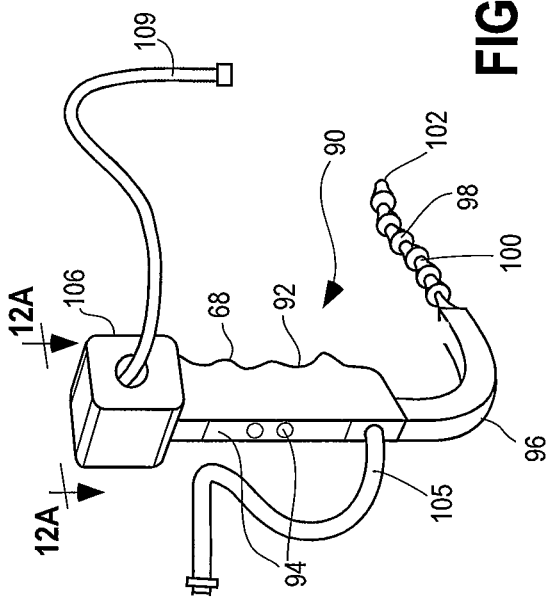
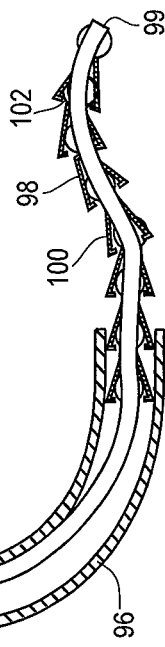
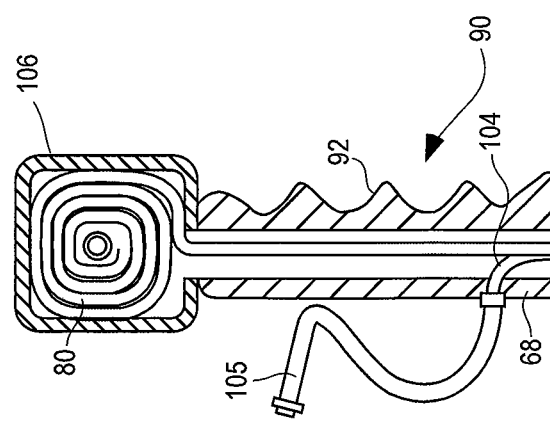

METHOD AND APPARATUS FOR DETERMINING OPTIMAL ENDOTRACHEAL TUBE SIZE

CROSS-REFERENCE TO RELATED APPLICATIONS

This application claims priority to U.S. Provisional Patent Application No. 62/000,182 filed May 19, 2014, the entire disclosure of which is incorporated herein by reference.

FIELD OF THE INVENTION

The present invention generally relates to endotracheal tubes. More specifically, the present invention relates to a method and apparatus for more accurately determining the optimal endotracheal tube size for safe and effective intubation and airway maintenance of any individual patient requiring placement of an endotracheal tube.

BACKGROUND OF THE INVENTION

When a patient is unable to breathe on his or her own due to a critical illness or injury, it becomes necessary for a clinician to place an endotracheal tube (also referred to herein as "ETT") into that patient's trachea to facilitate the patient's breathing. Similarly, when a patient is unable to breathe independently because s/he is under general anesthesia for surgery, it becomes necessary for a clinician to place an endotracheal tube into that patient's trachea to sustain the patient's breathing.

When preparing to manage a patient's airway, it is important to determine the correct size endotracheal tube for any individual patient for several reasons. As discussed in greater detail below, two parameters are critical—tube diameter and tube length. Tube diameter is measured relative to the narrowest diameter of the upper airway, the cricoid ring. However, the glottic aperture, a triangular shaped opening to the trachea, is defined by the true vocal cords and arytenoid cartilage and is located just proximal to the cricoid ring. The glottic aperture can be measured and the diameter of the cricoid ring can then be calculated. Tube length is measured relative to the distance between the patient's vocal cords and the carina of the trachea (a cartilaginous ridge within the trachea that runs antero-posteriorly between the two primary brochi at the site of the tracheal bifurcation at the lower end of the trachea).

For purposes of reference, two oppositely disposed ends of a tube shall be referred to as the machine end and the patient end, the machine end being the end that remains outside a patient's mouth for connection to a ventilation source (i.e. bag valve mask or mechanical ventilator), and the patient end being the end that is placed into the trachea. Also, for purposes of reference, the trachea can be divided into three theoretical zones. Zone 1 will be referred to as the Upper Trachea—Unsafe Positioning Zone. It is 3.1 cm long and is made up of the 1 cm long cricoid ring immediately below the vocal cords and a 2.1 cm length of the trachea. Research shows that if the machine end of the endotracheal tube cuff (balloon) encroaches on this region, increased risk arises for recurrent laryngeal nerve impingement or pressure directly applied to the vocal cords, either of which may lead to an increased risk for vocal cord injury and paralysis. Encroachment on this region also leads to an increased risk for unplanned extubation. Zone 2 is the Lower Trachea—Unsafe Positioning Zone. It is 2.0 cm long and if the tip of the tube encroaches on this region, an increased risk for endobronchial mal-positioning and associated complications arises. Zone 3 is the Safe Positioning Zone and lies between Zones 1 and 2.

If an endotracheal tube having too large a diameter (relative to the patient's glottic aperture) is placed through the glottic aperture, the force applied to the vocal cords may cause a subluxation or dislocation of the crico-arytenoid joints leading to vocal cord dysfunction. Too small a diameter tube may lead to air leaks and inadequate ventilation of the patient. Similarly, if an endotracheal tube whose length from the tip of the tube at the patient end (T) to the machine end of the balloon or endotracheal tube cuff ($B_{ME}$) (illustrated as T-$B_{ME}$ in FIG. 1) is too long relative to the length of the patient's tracheal Safe Positioning Zone, either the tip of the tube will encroach on the Lower-Trachea Unsafe Positioning Zone or the machine end of the inflated balloon will encroach on the Upper Trachea—Unsafe Positioning Zone. All of these conditions place the patient at risk for a number of complications arising from tube mal-positioning including pulmonary atelectasis, hypoxemia, pneumonia, pneumothorax, vocal cord injury, vocal cord paralysis, brain injury and death. To safely place an endotracheal tube in the proper position of the trachea, both the tip of the tube and the balloon must be positioned completely within the patient's Safe Positioning Zone.

Both the outside diameter (OD) of the tube relative to the diameter of the glottic aperture and the (T-$B_{ME}$) length of the endotracheal tube relative to the length of the Safe Positioning Zone should be known when determining the size of endotracheal tube that will be used to intubate a patient to minimize complications of endotracheal intubation and airway maintenance. Historically, however, endotracheal tube sizes and identification nomenclatures have been based solely upon the interior diameter (ID) of the endotracheal tube. Although it is important for the physician to determine the correct endotracheal tube size for every individual patient, most clinicians responsible for the intubation determine endotracheal tube size based upon an educated guess, rather than upon scientific formula, algorithm or accurate measurement of any kind. Some practitioners will choose to place a 7.5 mm endotracheal tube for all females and an 8.0 mm endotracheal tube for all males. Some will choose a 7.0 mm tube for small adults, a 7.5 mm tube for medium size adults and an 8.0 mm tube for large adults. Others may just get a so-called "feel" for the "appropriate" size tube they think a person may need based on their physical characteristics such as height, weight and general size appearance. No generally accepted and widely utilized method, formula, or system exists that maximizes the probability of choosing the optimally-sized endotracheal tube for adults.

In contrast, certain formulas and methods exist that are generally accepted and used by clinicians to calculate the "proper" size tube for insertion into neonates, infants and children. One generally accepted formula based on the age of the child is given as (ETT Size=4+age in years/4), and both weight-based and length-based systems are generally accepted and utilized to choose tube sizes in neonates, infants and children. However, even the weight and length-based systems that are considered the gold standard methods for choosing pediatric size tubes use indirect measures (weight/length) that do not correlate highly to nor predict well the tracheal length and glottic opening diameter and, thus, are not great predictors of optimal tube size.

As noted above, the size of an endotracheal tube is currently defined based on the inside diameter (I.D.) of the tube. Tube sizes range from a size 2.5 mm I.D. to a 10.5 mm I.D in 0.5 mm increments. However, endotracheal tubes with the same inside diameter (I.D.), have varying outside diameters (O.D.) depending upon the manufacturer and tube type. For instance, the Rusch 7.5 mm Standard ETT has an O.D. of 10.0 mm; the Mallinckrodt 7.5 mm Standard ETT has an O.D. of 10.2 mm; the Mallinckrodt 7.5 mm Hi-Lo Evac ETT has an O.D. of 11.2 mm; and the Teleflex 7.5 mm and the ISIS ETT each have an O.D. of 11.3 mm.

The International Organization for Standardization (ISO) requires that both the inside diameter (I.D.) and outside diameter (O.D.) be clearly marked on every endotracheal tube. Despite this reference to the outside diameter, most clinicians do not consider the outside diameter marking on the tube to determine the size of tube that will be utilized for any individual patient.

The ratio of the outside diameter of the endotracheal tube relative to the glottic aperture must be considered in order to minimize the risk for vocal cord injury. This ratio should be less than one. Preferably, the largest diameter endotracheal tube possible (which will minimize the "work of breathing") should be used while not placing a tube so large that it causes significant pressure on the vocal cords or dislocation of the arytenoid cartilages (leading to vocal cord dysmobility). Ensuring that the diameter of the ETT is smaller than the diameter of the glottic aperture will decrease the risk of vocal cord paralysis from arytenoid cartilage dislocation and other complications as noted hereinabove.

Historically in determining tube size based upon the diameter of the tube, the assumption is made that if the appropriate diameter tube is chosen, the appropriate length of tube automatically follows. However, determination of optimal endotracheal tube size for any individual patient should be based upon considerations of both diameter and length. More specifically, the clinician should consider not only the outside diameter of the ETT relative to the size of the patient's glottic aperture, but also should consider the T-$B_{ME}$ length relative to the VC-C length. The VC-C length is defined as the distance from a patient's vocal cords to the patient's tracheal carina. Every patient, based on his or her tracheal length, has a Safe Positioning Zone within the trachea, which defines the region within which both the endotracheal tube tip and balloon must be positioned.

In an attempt to protect patients from vocal cord injury from tubes whose T-$B_{ME}$ length is too long, ISO Standard 5361-1999 dictates to manufacturers the maximum allowable distance ($D_{MAX}$) from the tip of the patient end of an endotracheal tube to the machine end of the inflatable length of the tube's balloon. The ISO Standard $D_{MAX}$ for all size tubes is shown in Table 1. Because the maximum distance rather than the exact distance is defined in the ISO standard, this distance may vary for the same size tube from one manufacturer to another. The ISO Standard simply controls the T-$B_{ME}$ length for a given diameter tube. However, even if the clinician chooses a tube having the correct diameter tube, the T-$B_{ME}$ length may still be too long, despite ISO standards.

TABLE 1

ISO Standard for Max T-$B_{me}$ Distance (Dmax)

| I.D. (mm) | Dmax (mm) |
|---|---|
| 2.0 | — |
| 2.5 | — |
| 3.0 | — |
| 3.5 | — |
| 4.0 | — |
| 4.5 | — |

TABLE 1-continued

ISO Standard for Max T-$B_{me}$ Distance (Dmax)

| I.D. (mm) | Dmax (mm) |
|---|---|
| 5.0 | 56 |
| 5.5 | 56 |
| 6.0 | 58 |
| 6.5 | 62 |
| 7.0 | 66 |
| 7.5 | 69 |
| 8.0 | 72 |
| 8.5 | 75 |
| 9.0 | 78 |

In order to assist clinicians in placing an endotracheal tube at the correct depth, many manufacturers place a depth localizer band or marker on their endotracheal tubes. The depth localizer bands indicate the position of the tube that should be placed at the level of the vocal cords. Although ISO standards permit depth localizer markers on endotracheal tubes to provide assistance in positioning the tracheal tube within the trachea, no specific standards exist for the placement of these bands on the tube body. Moreover, no standards exist for determining VC-T distances for different size (I.D.) tubes.

As shown in FIG. 2, when the proper size (length) endotracheal tube is placed with the localizer band at the vocal cords, the tip of the tube as well as the entire balloon should be within the Safe Positioning Zone 46. This Safe Positioning Zone preferably places the tip (patient end of the tube) at least 2 cm above the carina to minimize the risk of endobronchial positioning of the tube, should the tube move either due to inadequate stabilization or due to flexion/extension of the patient's neck. It also preferably places the machine end of the inflated balloon at least 3.1 cm below the vocal cords, thus minimizing the risk of impingement of the recurrent laryngeal nerve and vocal cords as well as minimizing the risk of unplanned extubation.

Ensuring that both the tip of the tube and the entire balloon are within the Safe Positioning Zone of the trachea will minimize the risk of complications due to mal-positioning of the tube either at the time of placement of the tube or subsequently should any movement of the tube occur. If any of the T-$B_{ME}$ complex is too deep, the patient is at increased risk for endobronchial intubation and any of its inherent complications including hypoventilation, hypoxemia, pneumonia, and pneumothorax. If the T-$B_{ME}$ complex is too shallow, the patient is at increased risk for the inflatable balloon impinging on the recurrent laryngeal nerve and/or vocal cords and the inherent complications of vocal cord paralysis. In addition, if the T-$B_{ME}$ complex is too shallow, the patient is at increased risk for unplanned extubation and its inherent potentially deadly complications including vocal cord injury/paralysis, aspiration pneumonia, hypoxemia, brain injury and death.

The length of the trachea, from the upper end at the cricoid ring to the lower end at the carina varies in adults from approximately 10 cm to 15 cm with the average adult trachea measuring approximately 12.5 cm. FIG. 3 illustrates the importance of the VC-T and T-$B_{ME}$ distances when an endotracheal tube is placed. As shown in FIG. 3, a 7.5 mm ETT is positioned with the depth localizer bands at the vocal cords in (3A) a short trachea (10 cm), (3B) an average trachea (12.5 cm) and (3C) a long trachea (15 cm). Note that both the tip and the entire balloon of the 7.5 mm tube is within the Safe Positioning Zone 46 in both (c) the long trachea (15 cm) and (b) the average trachea (12.5 cm).

However, it is outside the Safe Positioning Zone 46 and at risk for endobronchial mal-positioning in (a) the short trachea (10 cm).

As shown in FIG. 4, when a 7.5 mm ETT is positioned in a patient with a short 10 cm trachea based upon the manufacturer depth localizer band properly placed at the vocal cords, the tip of the tube is noted to be too deep and is well within the Lower Trachea—Unsafe Positioning Zone, putting the patient at increased risk for endobronchial mal-positioning. If once the tip is noted to be too deep and the ETT is withdrawn several centimeters so that the tip of the tube is within the Safe Positioning Zone 46, then the machine end of the balloon encroaches on the Upper Trachea—Unsafe Positioning Zone, putting the patient at increased risk for impingement of the vocal cords and laryngeal nerve and increased risk for unplanned extubation. Therefore, a 7.5 mm ETT, manufactured under current diameter driven specifications, cannot be properly placed in any patient with a short trachea (10 cm) without putting the patient at increased risk for complications. Moreover, the diagrams in FIG. 5 illustrate that an individual with a short trachea (10 cm) cannot accommodate a tube larger than a 6.0 mm (FIG. 5D) with both the tube tip and balloon completely within the Safe Positioning Zone 46. Accordingly, the actual length of a patient's trachea should be determined to ensure that a tube with the correct lengths (VC-T and T-$B_{ME}$) is utilized and the length consideration should be separate from the diameter considerations discussed earlier.

In view of the foregoing, it will be apparent to those skilled in the art from this disclosure that a need exists for an improved method and apparatus for determining the optimal endotracheal tube size for safe intubation of a patient to minimize the risk for mal-positioning of the endotracheal tube and the complications associated therewith and that the optimal tube size must be based upon both tube diameter relative to the narrowest portion of the upper airway and length from the tip to the machine end of the balloon relative to the length of the patients trachea and Safe Position Zone. Moreover, a need exists for a method and device that accurately determines the limiting diameter of the patient's upper airway (cricoid ring/glottic aperture) as well as the length of the patient's trachea.

SUMMARY OF THE INVENTION

In order to achieve the above-mentioned objectives and other objects of the present invention, a method and an apparatus are provided to determine optimal endotracheal tube size based upon both an optimal tube length and optimal tube diameter for any individual patient requiring intubation therewith.

The above method and apparatus utilize a measurement device to determine the smallest diameter of a patient's airway by measuring the glottic aperture and then algorithmically determining the limiting diameter of the airway in order to determine the optimal outer diameter of the tube for any individual patient.

In one embodiment of the present invention, a measurement device may utilize indirect methods for determining the glottic aperture such as optical scanning, ultrasound, or any other indirect methods to measure the limiting diameter of the upper airway. The device may scan the glottic aperture and thereby determine the diameter of the opening of the glottis. The device may also scan the cricoid arch and measure the subglottic transverse diameter In an embodiment, the measurement device may also utilize methods to directly measure the glottic aperture such as a ring mandrel-type device directly deployed into the glottic aperture and cricoid arch.

In another embodiment, in addition to determining optimal tube diameter, a method and apparatus are provided which utilize a measuring device to determine the length of a patient's trachea and then algorithmically determine the optimal tube length for any individual patient. The measurement device employs indirect methods for determining the tracheal length such as ultrasound or other scanning devices. It may utilize associated external anatomical measurements to algorithmically determine the tracheal length, and it may employ direct measurement techniques that deploy a measuring tube directly into the trachea to determine the length thereof in a particular patient.

In an embodiment, an algorithm may be used with a machine, a processor or a computer to determine optimal endotracheal tube size by combining input data from demographics, by way of example, age, height, weight, and/or other anatomical measures, glottic diameter scan, subglottic transverse diameter scan and tracheal length scan.

In yet another embodiment, an apparatus is provided that includes a maneuverable arm, a fiber optic video guidance system and an introducer guide to maneuver an end of the apparatus around obstructions in a patient with a difficult airway to facilitate insertion of either an optimally sized ETT or a standard ETT into the patient's airway.

These and other objects of the present invention will become apparent to those skilled in the art from the following detailed description of preferred embodiments taken in conjunction with the accompanying drawings, figures and tables and by reference to the appended claims.

BRIEF DESCRIPTION OF THE DRAWINGS

Referring now to the attached drawings which form a part of this original disclosure:

FIG. 11 is a side sectional view of an apparatus for direct measurement of the length of a patient's trachea, as determined by the distance from the vocal cords to the carina (VC-C), by deploying an introducer tube with measuring capabilities in accordance with an embodiment;

FIG. 12A is a side sectional view of portions of an apparatus for intubation of a difficult airway caused by anatomical anomalies and/or obstructions in accordance with an embodiment;

FIG. 12B is a side perspective view of the apparatus of FIG. 12A in accordance with an embodiment;

FIG. 12C is a side elevation view of a fiber optic bundle element of the apparatus of FIGS. 12A and 12B;

FIG. 12D is a side perspective view of a cartridge element of the apparatus of FIGS. 12A and 12B;

DETAILED DESCRIPTION OF THE PREFERRED EMBODIMENTS

Selected embodiments of the present invention will now be explained with reference to the drawings. It will be apparent to those skilled in the art from this disclosure that the following descriptions of the embodiments of the present invention are provided for illustration only and not for the purpose of limiting the invention as defined by the appended claims and their equivalents.

Figure 1:
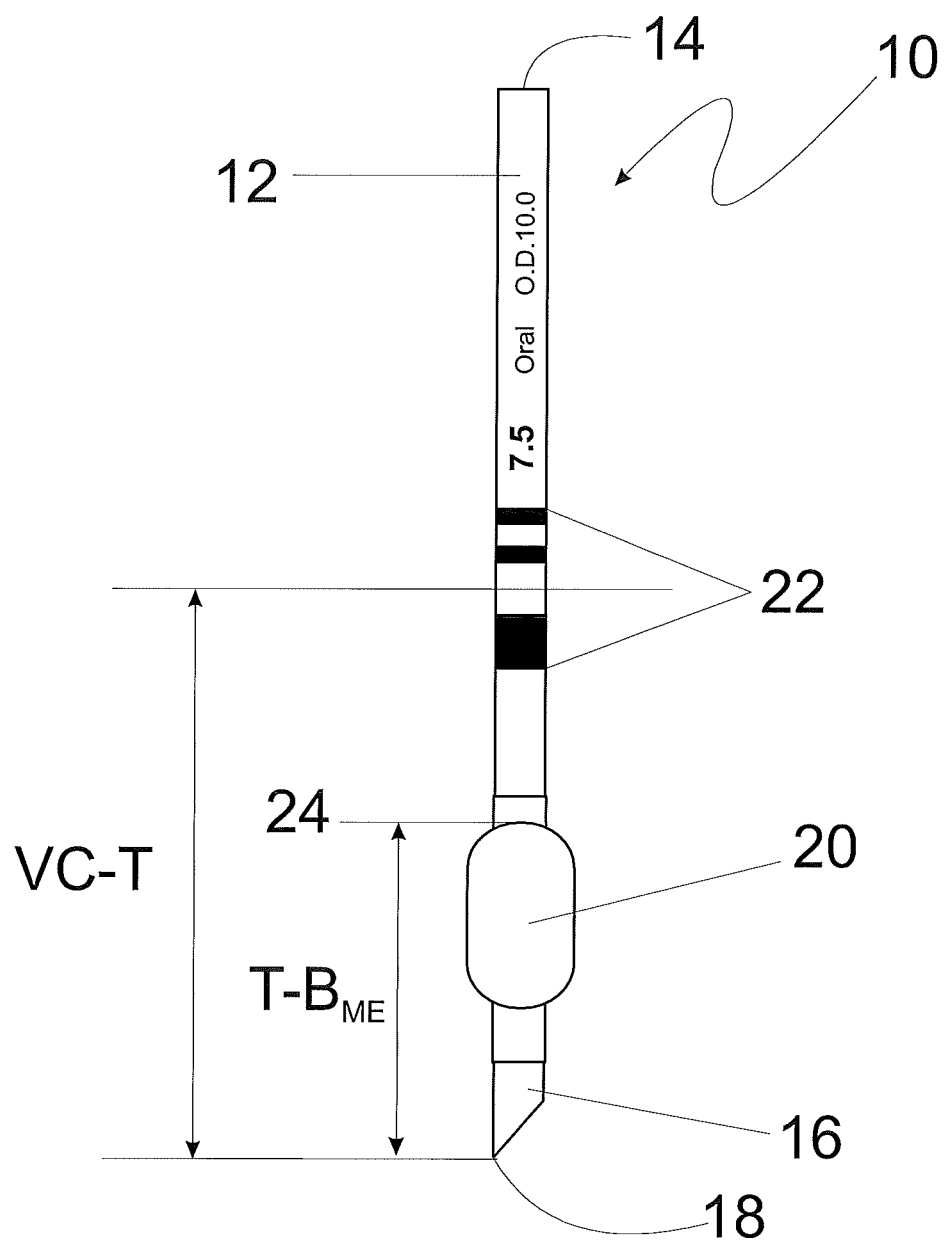
FIG. 1 is a side elevation view of an endotracheal tube ("ETT") illustrating the relative distances: 1. from a depth positioning marker on the tube (the position of the tube defined by the manufacturer that should be placed at the level of the vocal cords) to the tip of the patient end of the ETT (VC-T); and 2. the distance from the tip of the tube to the machine end of an inflatable balloon positioned on the tube (T-$B_{ME}$)

Referring now to FIG. 1, an endotracheal tube (ETT) of typical construction is shown at 10. The ETT includes a tubular body 12 having a proximal or machine end 14 and a distal or patient end 16. The distal end 16 includes a beveled tip 18 defined by the most distal part of the bevel to facilitate insertion into a patient's trachea (not shown). The ETT also includes an inflatable endotracheal tube cuff or balloon 20 to provide a seal between the ETT and the trachea after the tube is placed in the trachea, as is known in the art. The cuff or balloon may be adjustably inflated to a preselected pressure of sufficient magnitude to maintain the seal between the tube and the trachea, as will be described in greater detail below.

In accordance with current practice, the size of an endotracheal tube is defined based on the inside diameter (I.D.) of the tube. Tube sizes range from a size 2.5 mm I.D. to a 10.5 mm I.D in 0.5 mm increments, and The International Organization for Standardization (ISO) requires that both the inside diameter (I.D.) and outside diameter (O.D.) be clearly marked on every endotracheal tube. In the ETT shown in FIG. 1, by way of example, the tube is marked with size 7.5 indicating a 7.5 mm inside diameter. The O.D. size of 10.0 mm is also clearly marked. Depth positioning markers 22 placed on the tubular body by the manufacturer indicate the proper position of the tube at a patient's vocal cords and provide a reference point for measurement of the distance between the vocal cords and the patient end or tip of the tube 18, that distance being defined herein as VC-T. The distance from the patient end of the tube 18 to the machine end 24 of the inflatable balloon or cuff is indicated and defined by T-B$_{ME}$.

Figure 2:
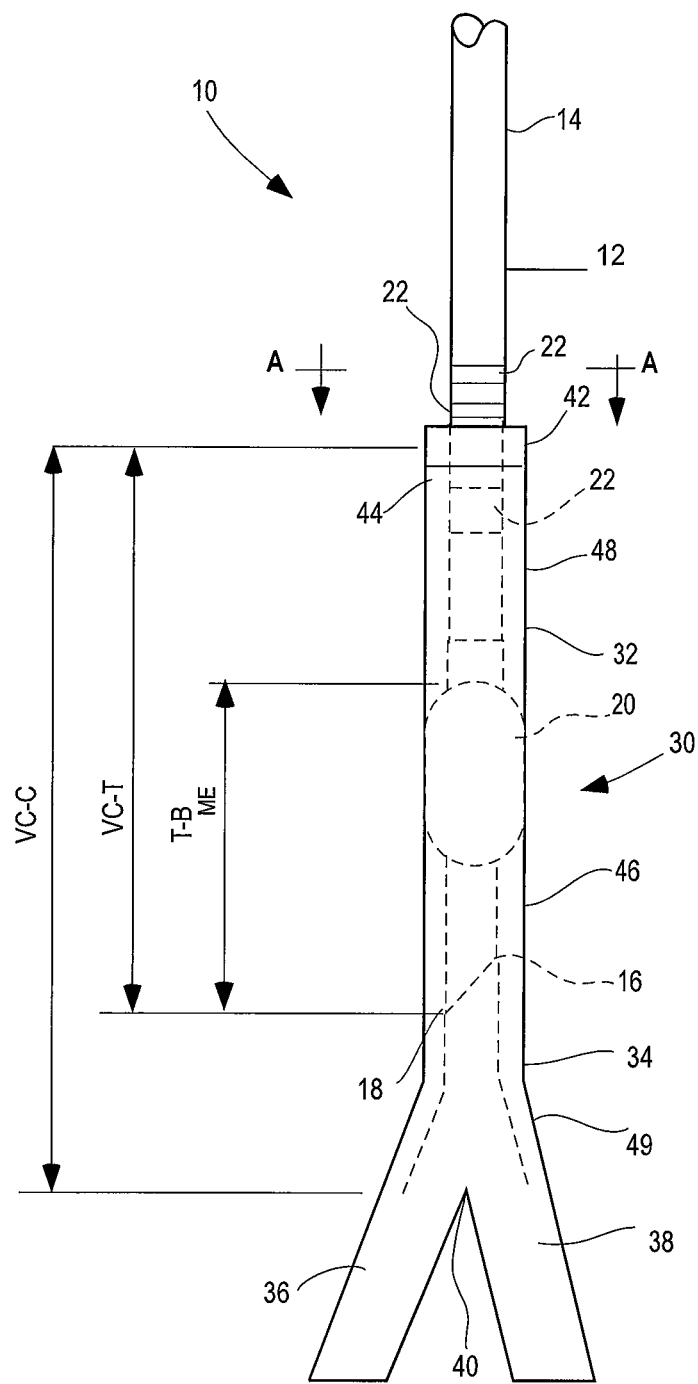
FIG. 2 is a side elevation view of an endotracheal tube situated with the tracheal anatomy of a patient, illustrating a Safe Positioning Zone and at least two Unsafe Positioning Zones.

FIG. 2 illustrates the ETT 10 placed in a patient's trachea shown in cross-section at 30. The trachea has a proximal or machine end 32 and a distal or patient end 34 from which the right and left bronchial tubes 36 and 38 separate into the patient's left and right lungs respectively at a ridge known anatomically as the carina 40. The patient's vocal cords or larynx 42 is positioned anatomically at the proximal end 32 of the trachea just above the cricoid cartilage or ring illustrated graphically at 44. Although not shown in the accompanying drawings, of critical importance to proper positioning of an ETT in an intubated patient is the location of the recurrent laryngeal nerve, the motor nerve to the vocal cords which lies near the cricoid ring. The Safe Positioning Zone 46, hereinafter sometimes referred to as the "SPZ," is the region within the trachea that both the tip of the tube and the entire balloon must be positioned to prevent complications of tube mal-positioning. Immediately above the Safe Positioning Zone is a region of increased risk of impingement of the balloon on the recurrent laryngeal nerve and vocal cords designated by the numeral 48 and which will be referred to herein as the Upper Trachea Unsafe Positioning Zone or Upper Trachea UPZ. Additionally, if the balloon is positioned with the Upper Trachea—Unsafe Positioning Zone, the tip of the tube will be located higher in the trachea and therefore closer to the vocal cords such that there is an increased risk of the tube mal-positioning above the vocal cords leading to an unplanned extubation. Immediately below the safe Positioning Zone is the Lower Trachea—Unsafe Positioning Zone 49 or Lower Trachea UPZ, a region of increased risk of endobronchial mal-positioning.

As discussed above, the SPZ 46 places the tip (patient end of the tube) 18 at least 2 cm above the carina 40 to minimize the risk of endobronchial positioning of the tube, should the tube move either due to inadequate stabilization or due to flexion/extension of the patient's neck. Similarly, the SPZ 46 places the machine end of the balloon at least 2 cm below the typical level of the recurrent laryngeal nerve and vocal cords to minimize the risk of both vocal cord injury and unplanned extubation.

Ensuring that both the tip of the tube and the entire balloon are within the Safe Positioning Zone 46, within the trachea 30, will minimize the risk of complications due to endobronchial intubation, unplanned extubation and impingement on the vocal cords 42 and recurrent laryngeal nerve lying near the cricoid ring 44. If the tip of the tube is too deep, the patient is at increased risk for endobronchial intubation and the inherent complications of endobronchial intubation including hypoventilation, hypoxemia, pneumonia, and pneumothorax (a collapsed or partially collapsed lung). If the tip of the tube is too shallow, the patient is at increased risk of the ETT balloon impinging the vocal cords or recurrent laryngeal nerve leading injury, vocal cord dysmobility, speech abnormalities and vocal cord paralysis. If the tip of the tube is too shallow, the patient is at increased risk for unplanned extubation and the inherent complications of unplanned extubation including vocal cord paralysis, aspiration pneumonia, hypoxemia, brain injury and death.

Figure 3:
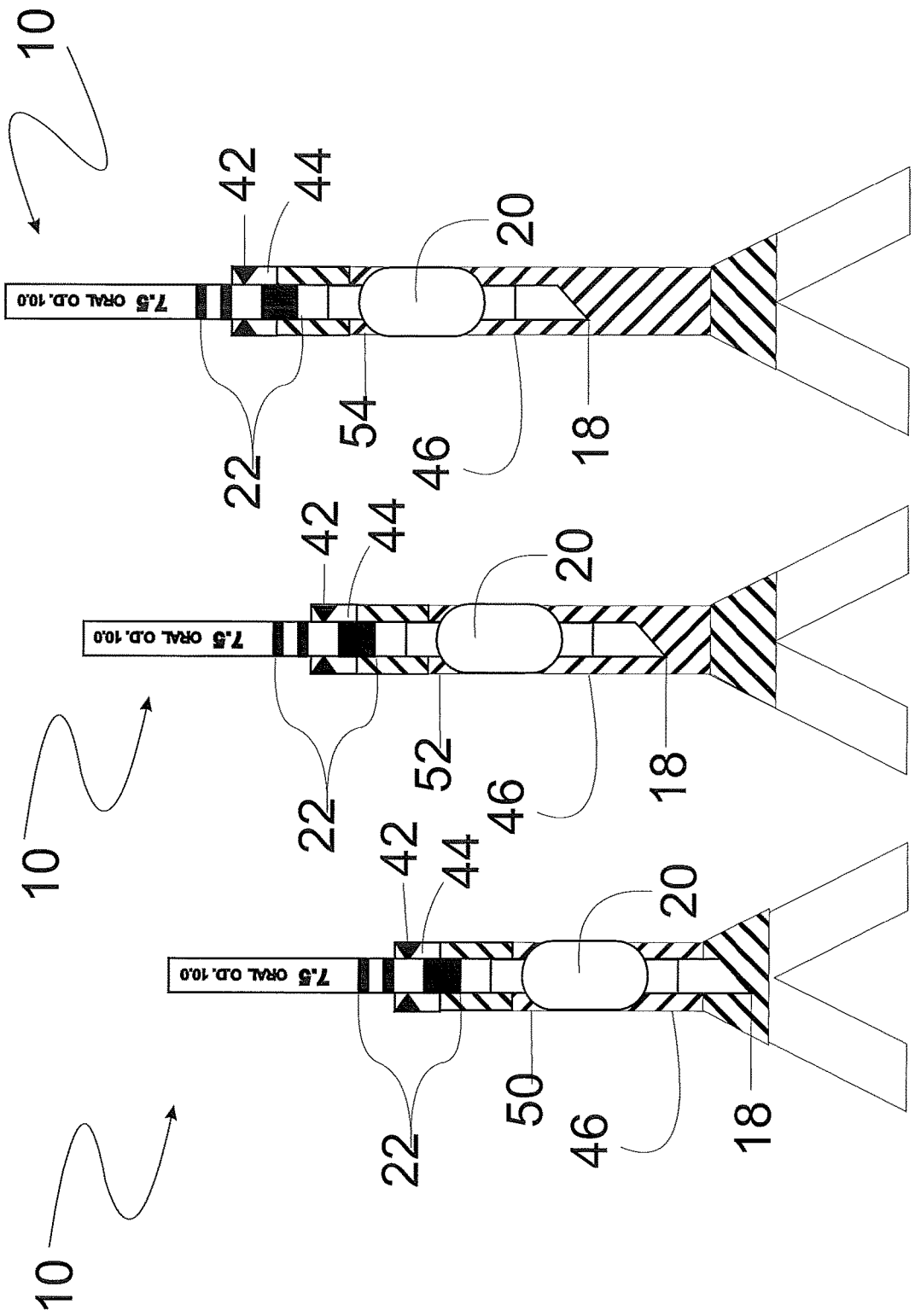
FIG. 3A is a side elevation sectional view along plane A-A of FIG. 2 of a 7.5 mm ETT positioned in the tracheal anatomy of an adult patient having a short tracheal length (approximately 10 cm) illustrating potential dangerous mal-positioning of the ETT tip in the short trachea.
FIG. 3B is a side elevation sectional view along plane A-A of FIG. 2 of a 7.5 mm ETT positioned in the tracheal anatomy of an adult patient having an average tracheal length.
FIG. 3C is a side elevation sectional view along plane A-A of FIG. 2 of a 7.5 mm ETT positioned in the tracheal anatomy of an adult patient having a longer than average tracheal length (15 cm)

FIGS. 3A-3C illustrate the importance of the VC-T and T-B$_{ME}$ distances and the Safe Positioning Zone, when an endotracheal tube is placed in a patient's airway. The length of the trachea as measured from just below the cricoid ring 44 to the carina 40 varies in adults from approximately 10 cm to approximately 15 cm. This length of the trachea in an average adult measures approximately 12.5 cm. The 7.5 mm ETT 10 illustrated in FIG. 1 is shown positioned with the depth localizer bands 22 at the vocal cords 42 in a short trachea 50 (10 cm), in FIG. 3A, average trachea 52 (12.5 cm) in FIG. 3B, and a long trachea 54 (15 cm) in FIG. 3C. Note that both the tip of the tube 18 and the balloon 20 are within the SPZ 46 in both the long trachea (15 cm) and the average trachea (12.5 cm); however, as shown in FIG. 3A, it is outside the Safe Positioning Zone and at risk for endobronchial mal-positioning in the short (10 cm) trachea 50.

Figure 4:
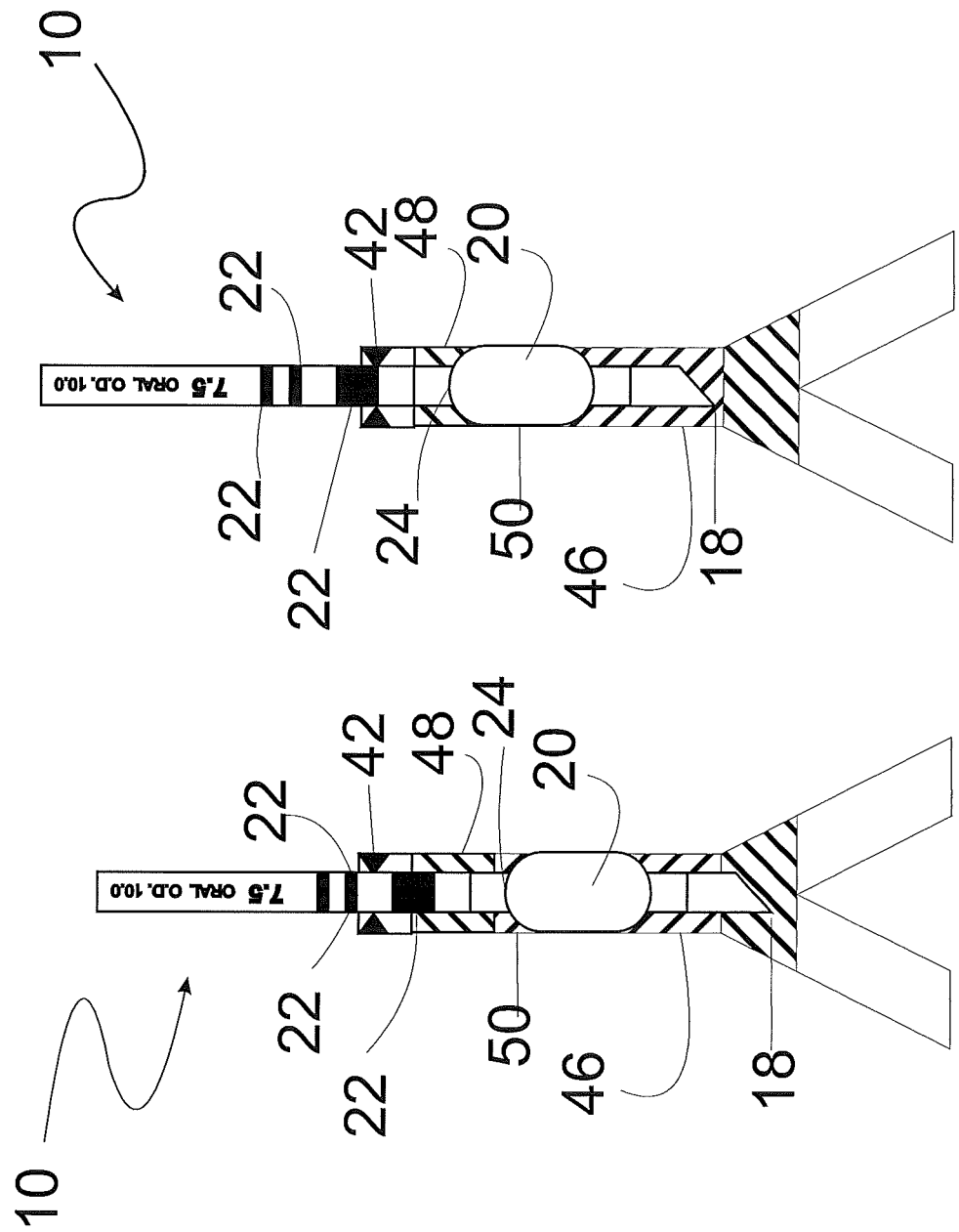
FIG. 4A is a side elevation sectional view along plane A-A of FIG. 2 of a 7.5 mm ETT positioned in a short (10 cm) trachea of a patient illustrating that an endotracheal tube that is too long for the length of a patient's trachea may result in the tip thereof being in an unsafe positioning zone.
FIG. 4B is a side elevation sectional view along plane A-A of FIG. 2 of the 7.5 mm ETT placed in FIG. 4A repositioned so that the ETT tip is within the safe positioning zone demonstrating, however, that the repositioning results in the machine end of the balloon encroaching on the upper Unsafe Positioning Zone.
Figure 5:
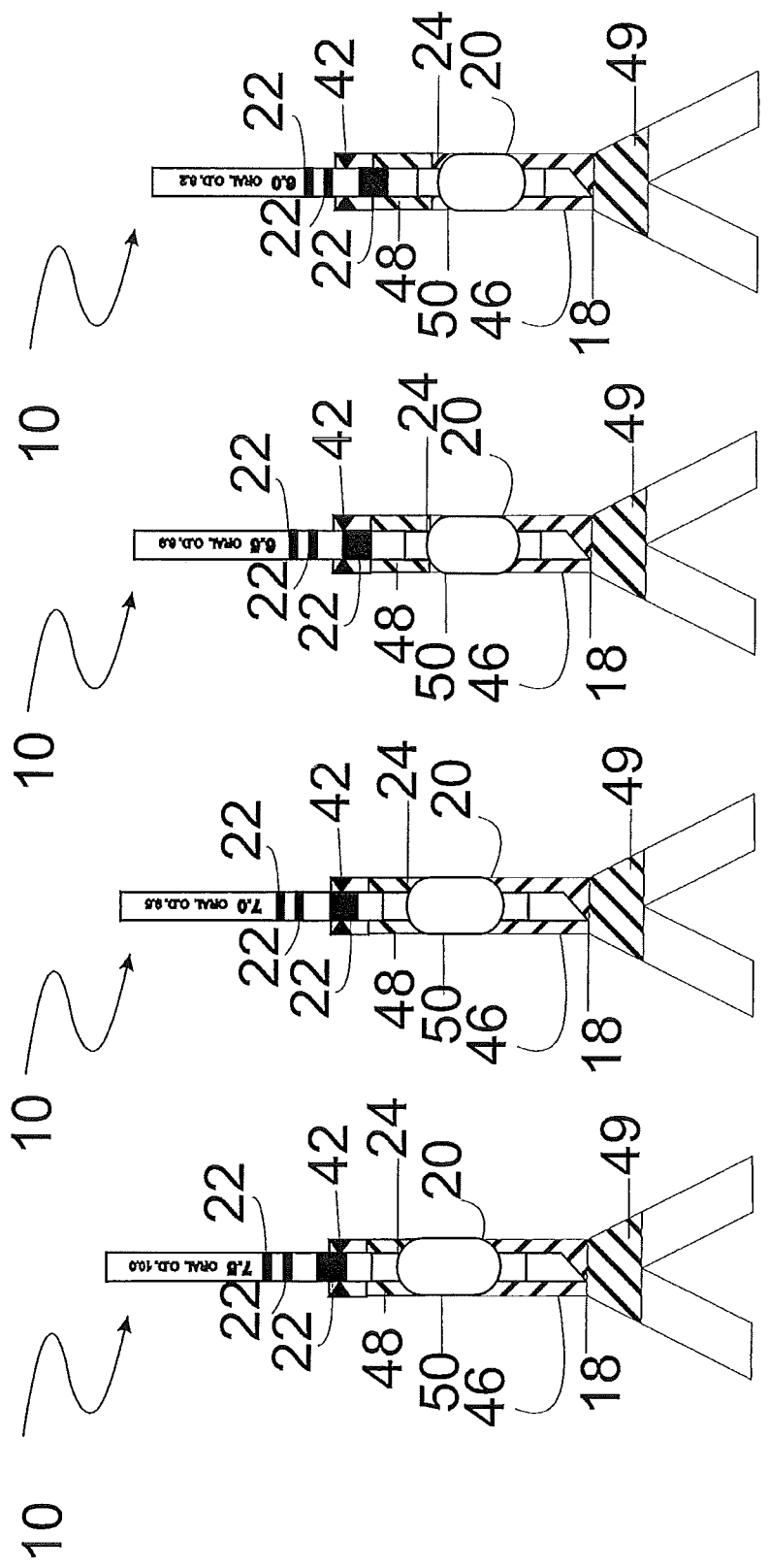
FIG. 5A is a side elevation sectional view along plane A-A of FIG. 2 of a 7.5 mm endotracheal tube positioned in a patient with a 10 cm trachea so that the tip of the ETT is just inside the Safe Positioning Zone. The machine end of the balloon encroaches on the Upper Unsafe Positioning Zone demonstrating that a 7.5 mm endotracheal tube cannot be safely positioned in a patient with a 10 cm trachea.
FIG. 5B is a side elevation sectional view along plane A-A of FIG. 2 of a 7.0 mm endotracheal tube positioned in a patient with a 10 cm trachea so that the tip of the ETT is just inside the Safe Positioning Zone. The machine end of the balloon encroaches on the Upper Unsafe Positioning Zone demonstrating that a 7.0 mm endotracheal tube cannot be safely positioned in a patient with a 10 cm trachea.
FIG. 5C is a side elevation sectional view along the plane A-A of FIG. 2 of a 6.5 mm endotracheal tube positioned in a patient with a 10 cm trachea so that the tip of the ETT is just inside the Safe Positioning Zone. The machine end of the balloon encroaches on the Upper Unsafe Positioning Zone demonstrating that a 6.5 mm endotracheal tube cannot be safely positioned in a patient with a 10 cm trachea.
FIG. 5D is a side elevation sectional view along the plane A-A of FIG. 2 of a 6.0 mm endotracheal tube positioned in a patient with a 10 cm trachea so that the tip of the ETT is just inside the Safe Positioning Zone. The machine end of the balloon is within the Safe Positioning Zone demonstrating that a 6.0 mm endotracheal tube can be safely positioned in a patient with a 10 cm trachea.

Referring now to FIGS. 4A and 4B, the situation may be further complicated when a 7.5 mm ETT 10 in a patient with a 10 cm trachea is withdrawn several cms so that the tip 18 is within Safe Positioning Zone 46. As shown in FIG. 4B, the machine end 24 of the cuff 20 then encroaches on the Upper Trachea UPZ 48, the region of increased risk for impingement of the vocal cords and laryngeal nerve and increased risk for unplanned extubation. The intuitive solution would be for the clinician to use the next smaller size (7.0 mm) to eliminate the increased risks to the patient. However, as shown in FIGS. 5A-5D, an individual with a short (10 cm) trachea 50 cannot accommodate a tube larger than a 6.0 mm with both the tube tip 18 and the machine end 24 of the balloon within the Safe Positioning Zone 46. If a tube larger than 6.0 mm is chosen, either the machine end of the tube will encroach on the Upper Trachea UPZ 48 or the tip 18 will encroach on the region of increased risk for endobronchial mal-positioning or Lower Trachea UPZ 49. This clearly demonstrates that the actual length of a patient's trachea should be determined to ensure that a tube is used which has not only the correct diameter to avoid laryngeal injury, as discussed in greater detail above, but also the correct length (VC-T and T-B$_{ME}$) to avoid the complications of tube mal-positioning.

Figure 6:
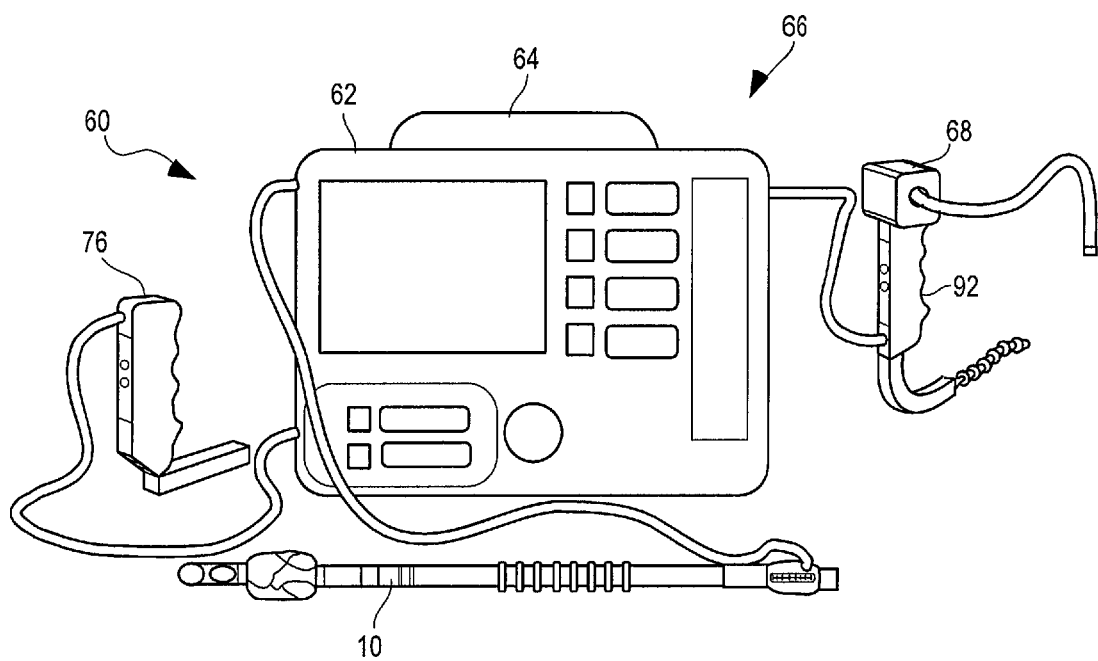
FIG. 6 is a diagrammatic view of an UltraSafe Airway Management System Device which includes airway monitoring equipment and an ETT optimal size determination apparatus illustrating the elements thereof in accordance with an embodiment of the present invention.

Referring now to FIG. 6, an endotracheal tube optimal size determination apparatus in accordance with an embodiment of the present invention is shown generally at numeral 60. The apparatus can be a standalone device used simply to determine the optimal tube size for any patient under consideration for endotracheal intubation, or it can be combined with other critical electrocardiogram (EKG), heart rate (HR) or non-invasive blood pressure (NIBP) monitoring equipment and airway safety monitoring equipment. By way of example and not of limitation, such safety monitoring equipment may include systems for monitoring EtCO$_2$ (end-tidal CO$_2$ or the level of carbon dioxide present at the end of an exhaled breath), SaO$_2$ (the saturation level of oxygen in hemoglobin), cardiac rhythm, and/or apparatus for monitoring and adjusting cuff or balloon pressure such as disclosed in U.S. patent application Ser. No. 13/924,568 filed Jun. 22, 2013 by the inventor of the instant invention.

The apparatus 60 includes various attachments and devices which will be discussed in greater detail below to perform the following functions to carry out the steps of the novel methods of the present invention to ensure that an ETT of both the proper diameter and length is selected for safe intubation of any patient:

1. Indirect measurement of critical anatomical parameters of a patient's tracheal and glottic physiology.
      a. Ultrasound imaging device scans and measures tracheal length parameters.
      b. Glottic aperture measurement.
         1) Optical scan to measure glottic aperture which may be combined with a fiberoptic video laryngoscope to facilitate determination of ETT size as an integral part of the process of fiberoptic video intubation.
         2) Ultrasound imaging scan of the cricoid arch (measures subglottic diameter).
   2. Direct measurement of critical anatomical parameters of a patient's tracheal and glottic physiology.
      a. Introducer placed during intubation process that directly measures tracheal length
      b. Graduated cone measurement device to directly measure the glottic aperture.

Referring to FIG. 6, the apparatus 60 includes a portable housing or body 62 structured and arranged to enclose and protect system electronics and analytical software, computers, processors and associated subsystems necessary for performing analyses and algorithmic calculations in response to indirect and direct anatomical measurements as hereinabove described to determine proper ETT size. By way of example, the indirect and/or direct anatomical measurements may be combined with demographically-collected and statistically compiled data such as age, height, weight and anatomical measurements such as tracheal length, glottic diameter, subglottic transverse diameter and the like, and analyzed by the apparatus' analytical systems to determine proper ETT size.

Figure 7:
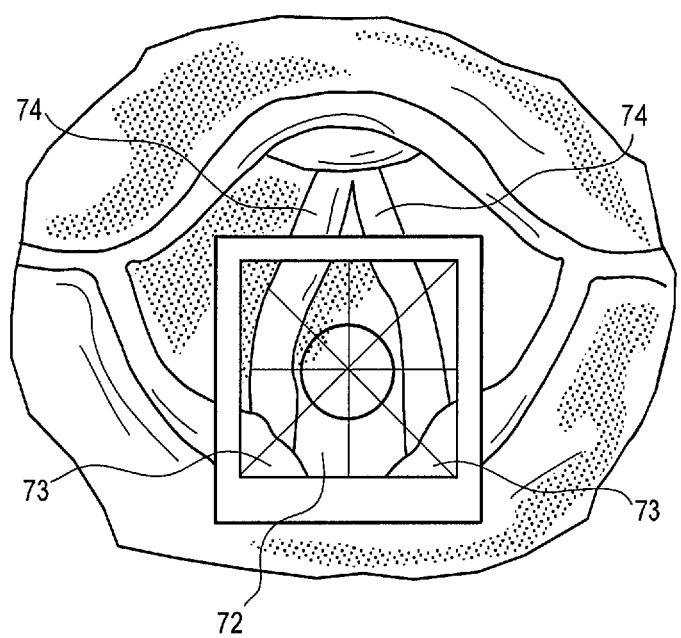
FIG. 7 is a cross-sectional view of a patient's airway taken immediately above the vocal cords illustrating an optical scanning method of indirect measurement of a patient's glottic aperture in accordance with an embodiment.
Figure 8:
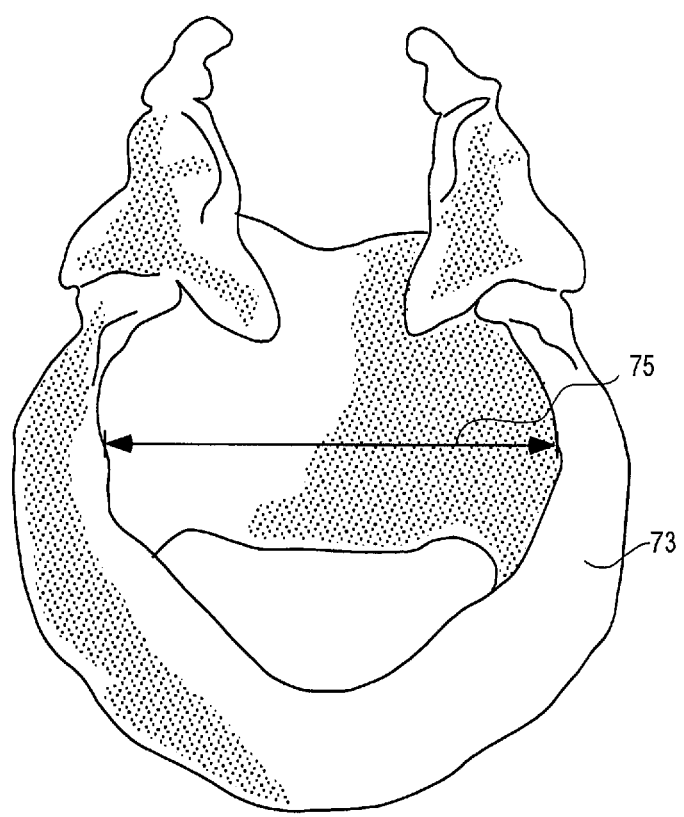
FIG. 8 is a diagram of the cricoid cartilage.
Figure 9:
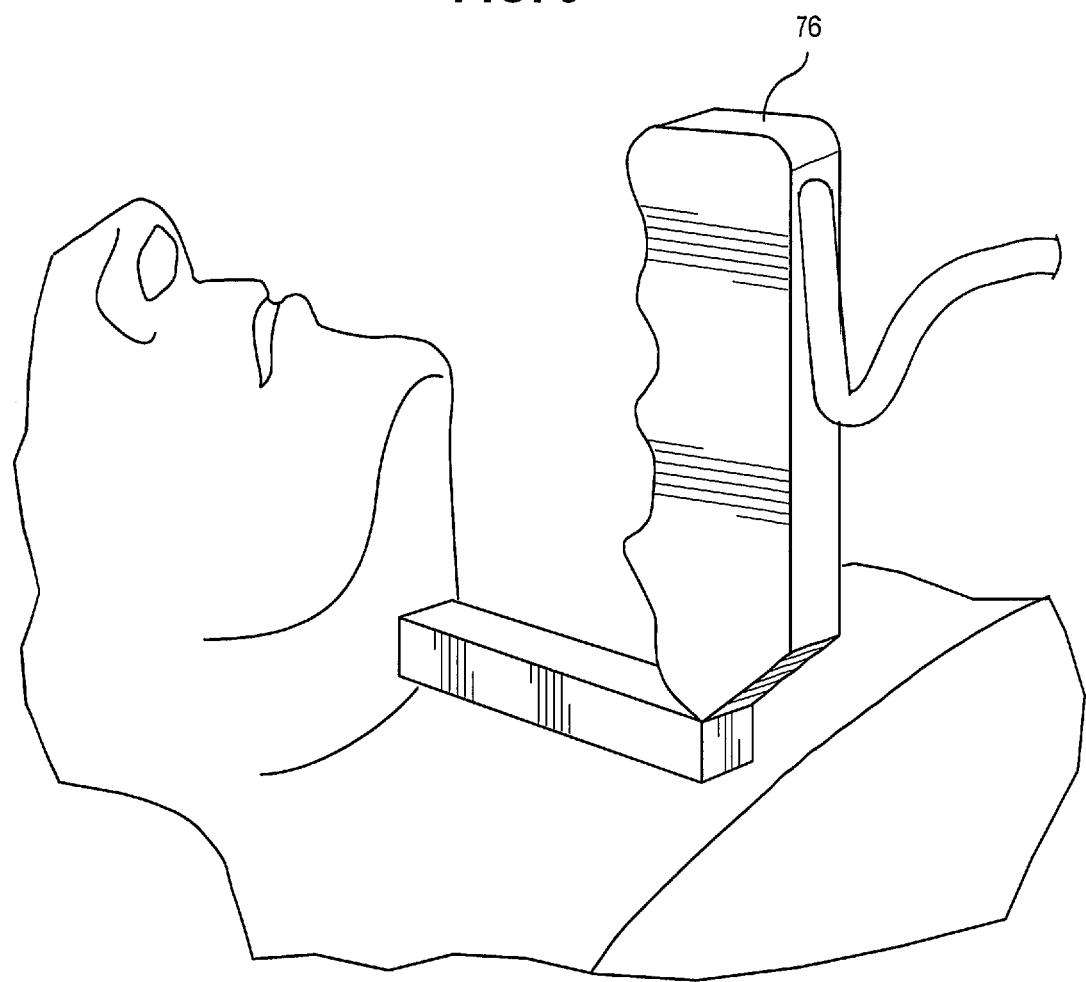
FIG. 9 is a side perspective view of an apparatus for ultrasonic indirect measurement of the length of the trachea shown in position on a patient.

The housing includes a carrying handle 64 secured thereto for ease of transporting the apparatus for field use by aeromedical flight teams and field paramedics. Various scan, test and control dials, selection buttons, input and output connection ports, and readout screens as known in the medical instrumentation art are illustrated generally at 66. The apparatus 60 includes, by way of illustration and not of limitation, an optical and/or ultrasound scanning device as part of a hand-held intubating video laryngoscope, shown generally at 68, for generating indirect images for measurement of the glottic aperture during intubation. By way of example and not of limitation, FIG. 7 shows an optical scanning screen image 70 overlaying a glottic aperture 72 formed by the vocal cords 74 and cricoid or arytenoid cartilage 73. The intubating laryngoscope shown at 68 and described in greater detail in FIGS. 11 and 12 can also use its ultrasound scanning capabilities to measure the length of the vocal cord to carina distance during the intubation process. An ultrasound scanning device 76 is connected to the apparatus for generating indirect images of the cricoid arch for measurement of the subglottic aperture diameter 75 shown in FIG. 8 and for generating indirect ultrasound images of the trachea for measurement of tracheal length. FIG. 9 shows the ultrasound scanning device 76 positioned on a patient's thoracic area and adapted to measure indirectly via ultrasonic energy the length of the patient's trachea.

Figure 10:
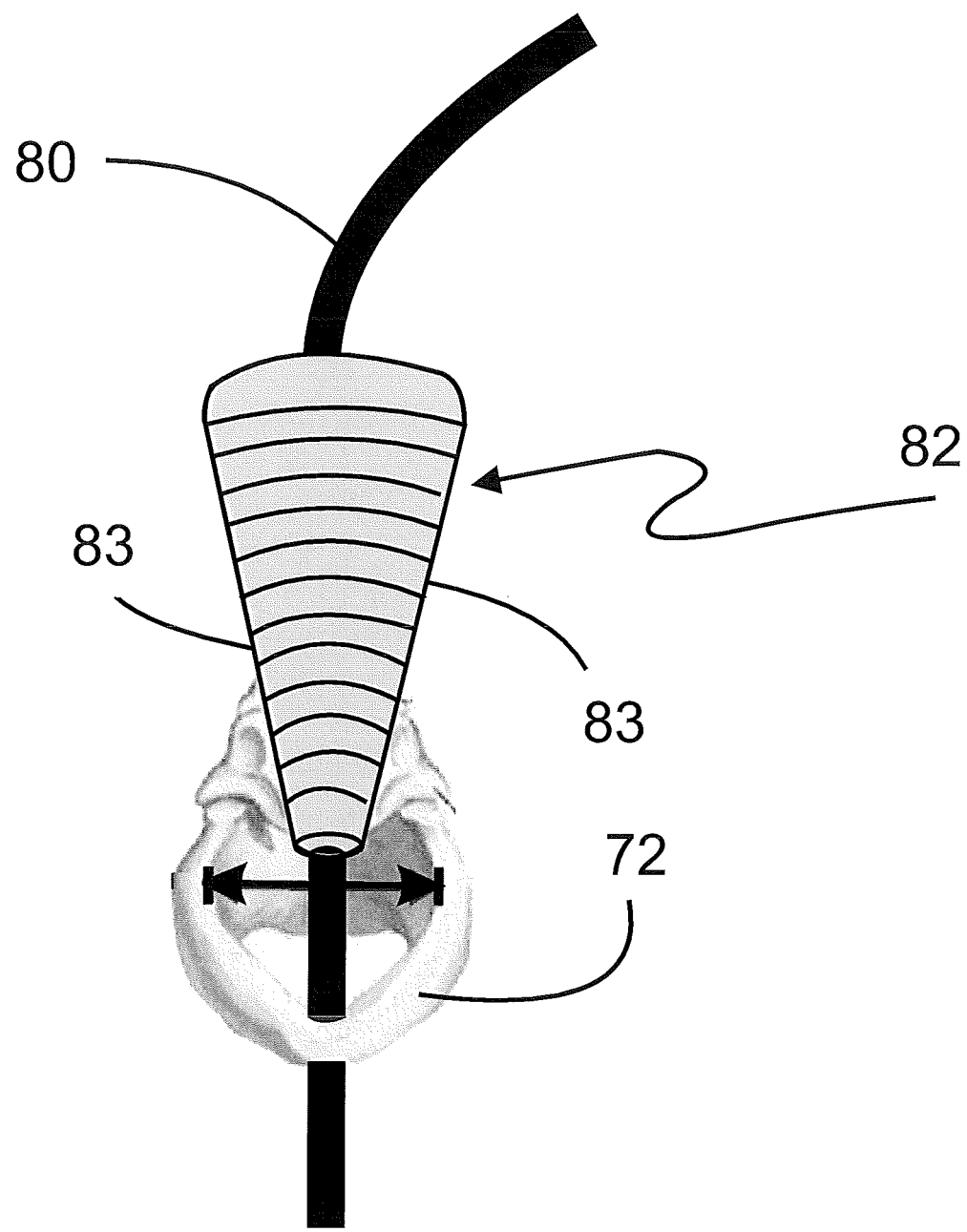
FIG. 10 is a side elevation view of a ring mandrel device deployed over an introducer extending into the cricoid cartilage shown in FIG. 8 illustrating a direct method of measuring a patient's glottic aperture in accordance with an embodiment.

Directing the reader's attention now to FIGS. 10 and 11, separate devices are shown for direct measurement of critical anatomical parameters of a patient's tracheal and glottic physiology. FIG. 10 illustrates a guide mechanism or introducer 80 adapted to be inserted into a patient's trachea during the measuring and intubation process, as will be discussed in greater detail below. A ring mandrel or graduated cone measurement device 82 is deployed over the introducer 80 and structured and arranged to directly measure the glottic aperture 72. By way of example and not of limitation, the mandrel or cone may have graduated rings 83 formed therein of predetermined diameters and/or pressure sensors affixed thereto at various intervals to indicate where it engages the glottic aperture to obtain the size thereof. Alternatively, a fiber optic device may be inserted simlutaneously and coaxially therewith to obtain a visual reading of the contact point to properly determine the size of the aperture 72.

To measure the tracheal length directly, an introducer 80 may be inserted via the hand-held intubating video laryngoscope 68 having a video laryngoscope tip or end portion 85 placed during the intubation process that directly measures tracheal length, as best shown in FIG. 11. Once the video laryngoscope tip 85 is positioned at the vocal cords 74, the introducer is extended until the end 87 thereof is at the level of the carina 40. The length of tube that is extended to reach from the vocal cords 72 to the carina 40 is measured by the video laryngoscopic intubator 84. The introducer 80 may have measurement graduations or markings formed thereon whereby the length of introducer extended to reach the carina 40 may be read through the video laryngoscope. Alternatively, the length of introducer extended from the intubator 84 to reach the carina 40 can be directly measured by the video laryngoscopic intubating device as the introducer tube is extended.

Figure 13A:
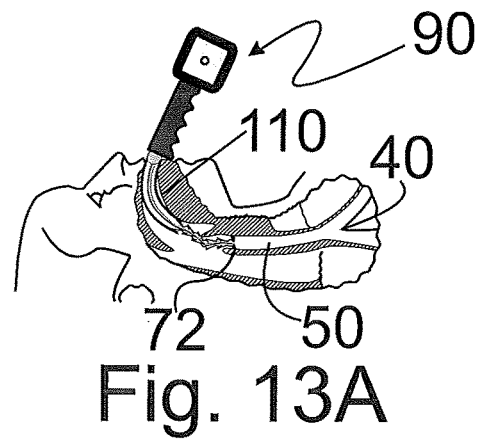
FIGS. 13A-13E illustrate visually the steps of a method for intubation of a difficult airway using the apparatus of FIGS. 12A-12D.
Figure 13B:
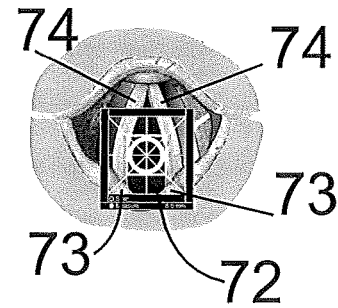
Figure 13C:
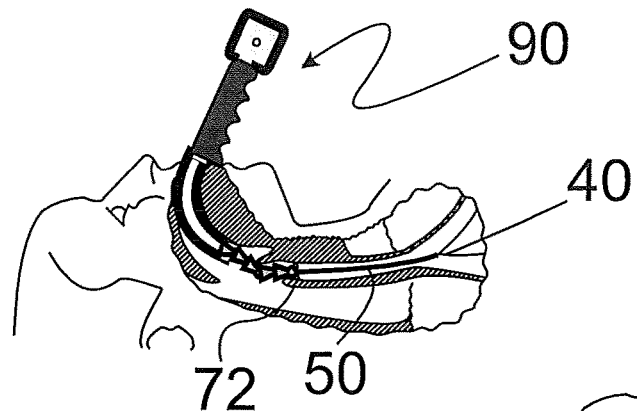
Figure 13D:
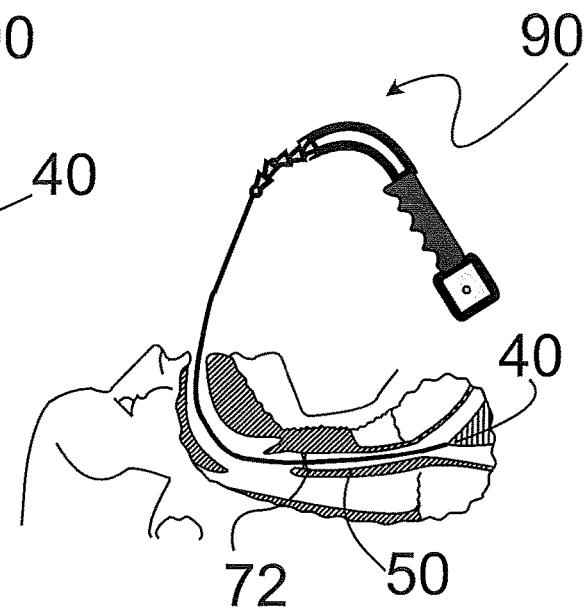
Figure 13E:
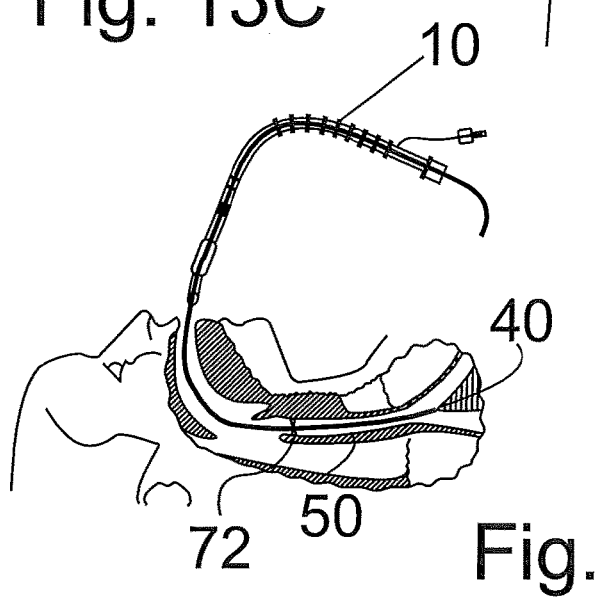
Figure 14:
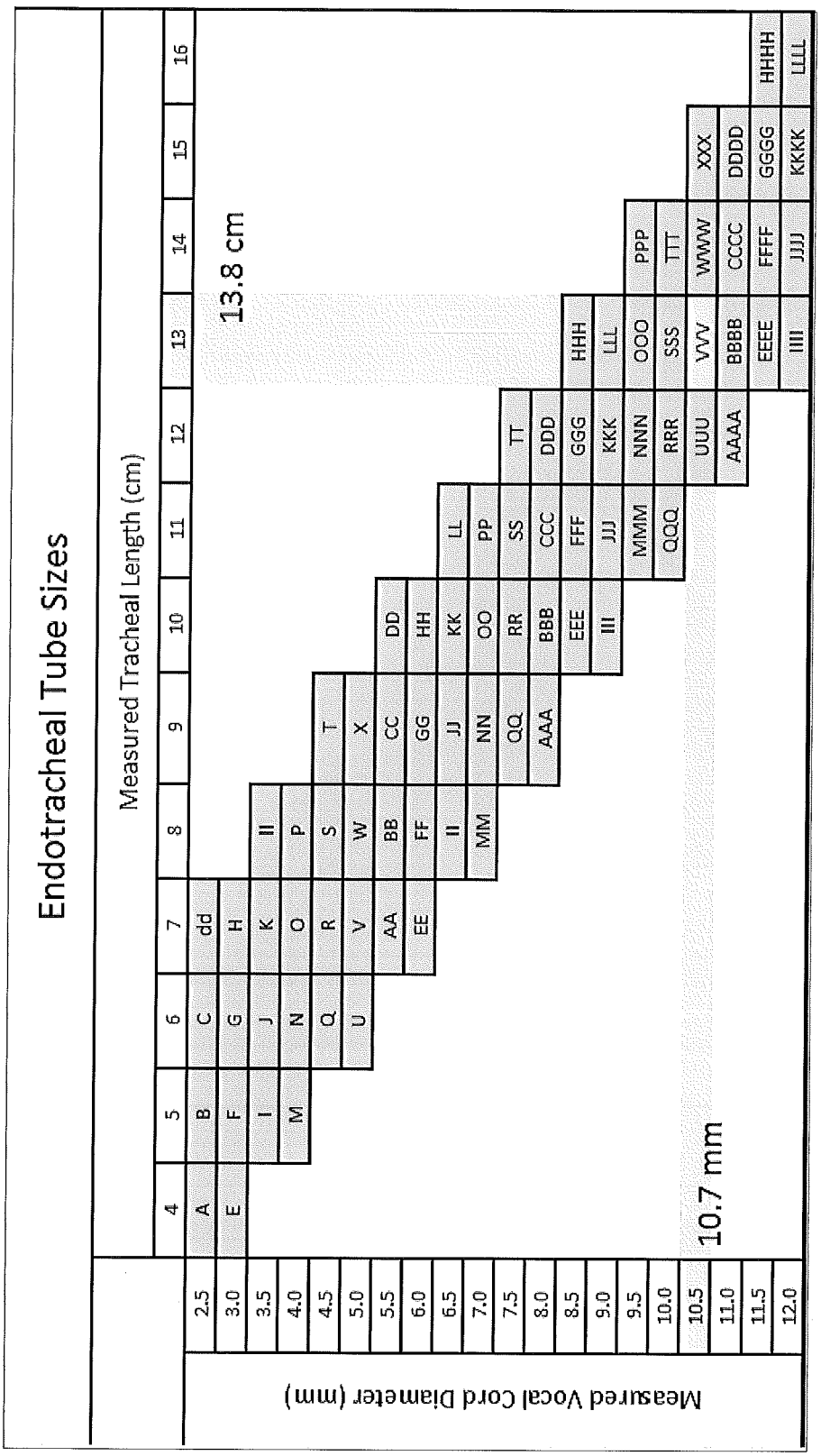
FIG. 14 is a table illustrating graphically optimal ETT sizes as a function of measured vocal cord diameter and measured tracheal length in accordance with an embodiment.

Referring now to FIGS. 12-14, an apparatus 90 for intubation of a difficult airway, also referred to herein as a difficult airway intubator, is shown. A difficult airway is one that, due to anatomical variations or medical/trauma issues makes passing an endotracheal tube through the glottic aperture "difficult". Sometimes the difficult airway is of such severity that it makes passage of an endotracheal tube by standard means of intubation nearly impossible. Therefore, the difficult airway intubator 90 of the instant invention is designed to deal with those anatomical anomalies or obstructions caused by medical issues suchs as tumors or trauma issues such as severe swelling.

As shown in greater detail in FIGS. 12A-D, the difficult airway intubator 90 includes the hand-held intubating video laryngoscope 68 shown in FIG. 6. The laryngoscope has a handle portion 92; a curvilinear blade 96 for insertion into a patient's oral cavity and extension into a patient's posterior pharynx; a flexible intubation arm 98 having a hollow core 99 extending coaxially along the the length thereof comprising a series of sections 100 each sequentially connected to one another by a plurality of extensible, rotatable joints 102; a fiber optic video/ultrasound bundle 104, the fiber optic video to aid in visually guiding the intubation arm 98 into the patient's trachea and the ultrasound device used to measure the length of the trachea; a semi-flexible, hollow tube or introducer 80 which can be extended into the trachea, over which an endotracheal tube is placed to be guided into the trachea during intubation as illustrated in FIG. 13 A-E, The hollow portion of the introducer can be connected to an oxygen source and utilized as a oxygen delivery system directly into the trachea during the intubation process. A plurality of controls 94 on the handle manipulate the flexible intubation arm enclosing the coaxially extending fiber optic bundle and the introducer/oxygen delivery tubes so that it can be maneuvered around obstructions which may be present in the patient's oral cavity to allow for a clear view of the patient's vocal cords 74 as best shown in FIG. 13B. The fiber optic bundle is connected through the video laryngoscope handle 92 to the video monitor 60 (FIG. 6) via a fiber optic bundle cable 105.

In another embodiment, a second fiber optic bundle 101 can be mounted on the curvilinear blade 96 and attached to the video monitor through cable 105 to allow for continuous viewing of the movement of the flexible intubation arm 98 relative to its position in the oral pharynx and vocal cords. The secondary fiber optic video will allow for continued viewing of the vocal cords/intubation arm/introducer even when the primary fiber optic bundle 104 is deployed into the trachea.

In addition, the apparatus 90 of the present invention addresses a problem associated with current intubation devices/methods. Specifically, once the vocal cords are exposed with a video laryngoscope, the endotracheal tube must then be maneuvered separately around the same obstructions with a clinician's right hand while the view of the cords is maintained in the video laryngoscope with the clinician's left hand. The difficult airway intubator 90 herein disclosed solves that problem by incorporating a detachable sterile cartridge 106 having an introducer 80 stored therein and being selectively extendable via controls 94 through handle portion 92 and curvilinear section 96 into the longitudinally extended core 99 of the intubation arm 98, thereby allowing for manual deployment of an introducer 80 through the tip 103 of the intubator and into the trachea 50, once the tip is aligned with the glottic aperture. Once the introducer 80 is deployed into the trachea 50 it can be used to guide the endotracheal tube 10 around any obstructions, through the vocal cords and into the trachea. The secondary fiberoptic 101 can be used to view the endotracheal tube passing through the cords and into the trachea. The introducer may also be adapted to deliver oxygen to the patient via a separate tube 109 within the core of the introducer. As the patient is being intubated, oxygen is continuously delivered through the core of the introducer.

In operation, the difficult airway intubator 90 would be introduced into a patient's oral cavity 110 as shown in FIG. 13A. Through fiber optic video visualization of the oral airway, the tip 103 of the intubation arm and flexible portion 98 would be segmentally adjusted and advanced around any obstructions or anatomical anomalies until the tip 103, is located at the glottic aperture 72 as shown in FIG. 13A. Once the tip 103 is at the glottic aperture 72 an optical scan or ultrasound of the vocal cord diameter can be measured as shown in FIG. 13B. Then the introducer 80 and fiber optic bundle 104 are advanced into the trachea 50 until it reaches the carina 40, FIG. 13C. With the tip of the introducer 80 at the carina 40 a measure of trachea length can be taken. Once both vocal cord diameter and tracheal length measures are completed the video laryngoscopic intubator 90 is removed leaving the introducer 80 in the trachea, FIG. 13D. An endotracheal tube 10, of specific size for the individual patient as determined by the vocal cord diameter and tracheal length measures taken previously, is then placed over the introducer 80 and advanced until properly seated in the trachea as shown in FIG. 13E.

In another embodiment, once the introducer is positioned as shown in FIG. 13 C, rather than completely removing the intubator 90 to allow for placement of the endotracheal tube 10 over the end of the introducer, the introducer 80 can be separated from the intubator with the intubator remaining in place. In this manner, the intubator with its secondary fiber optic 101 near the glottic aperture will allow for direct visualization of the ETT as it is passed over the introducer 80, through the vocal cords 72 and into the trachea 50. By example, and as illustrated in FIG. 14, if a patient's vocal cord diameter measured 10.7 mm and their tracheal length measured 13.6 cm, the optimal size determination device would indicate the optimal tube to be a size VVV. This tube would be optimally designed (I.D., O.D., VC-T, T-B$_{ME}$, and tube length for a patient with the above measurements.

GENERAL INTERPRETATION OF TERMS

In understanding the scope of the present invention, the term "configured" as used herein to describe a component, section or part of a device that is constructed to carry out the desired function. In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including," "having" and their derivatives. Also, the terms "part," "section," "portion," "member" or "element" when used in the singular can have the dual meaning of a single part or a plurality of parts. Finally, terms of degree such as "substantially," "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents.

What is claimed is:

1. An apparatus for intubating a patient with an endotracheal tube, the endotracheal tube being adapted to be inserted in a trachea of a patient requiring intubation, the patient having a head, a face, a mouth, an oral cavity, a thoracic area, a trachea having a length and forming an airway in the patient, vocal cords, a cricoid arch cooperating with the patient's vocal cords in forming a glottic aperture, and a carina defining a point at which the trachea separates into a left and a right bronchial tube, the apparatus comprising:
   a hand-held intubating laryngoscope operatively connected to a handle and a detachable sterile cartridge, the laryngoscope including a curvilinear blade adapted to be inserted into the patient's oral cavity, the handle having a plurality of controls positioned thereon; the detachable sterile cartridge operatively connected to the handle, the detachable sterile cartridge being adapted to store a semi-flexible, hollow guide tube or introducer, wherein the curvilinear blade contains an extendable flexible intubation arm therein; the extendable flexible intubation arm including a hollow core extending coaxially along a length thereof, the extendable flexible intubation arm comprising a plurality of sections, each one of the plurality of sections being sequentially connected to an adjacent one of the plurality of sections by one of a plurality of extensible, rotatable joints, and a tip; and
   a fiber optic video and ultrasound bundle having a fiber optic video portion and an ultrasound portion, wherein the fiber optic video portion of the bundle is adapted to aid in visually guiding the flexible extendable intubation arm into the patient's oral cavity; and wherein the ultrasound portion of the bundle is adapted to measure the length of the patient's trachea, wherein the fiber optic video and ultrasound bundle positioned within the extendable flexible intubation arm; and
   the semi-flexible, hollow guide tube or introducer having measuring capabilites and being adapted to be deployed into the patient's trachea by sliding through a channel of the extendable flexible intubation arm and configured to be removed from the extendable flexible intubation arm, the curvilinear blade, and the handle to facilitate intubation of the patient with an endotracheal tube by guiding the endotracheal tube into the patient by passing the endotracheal tube over the introducer.

2. The apparatus of claim 1, wherein the apparatus further includes a device for measuring a diameter of the glottic aperture.

3. The apparatus of claim 2, wherein the device for measuring the diameter of the glottic aperture comprises a ring mandrel.

4. The apparatus of claim 2, wherein the device for measuring the diameter of the glottic aperture comprises an optical scanning device.

5. The apparatus of claim 2, wherein the device for measuring the diameter of the glottic aperture comprises an ultrasound scanning device.

6. The apparatus of claim 1, wherein the endotracheal tube includes a cuff which is adjustably inflatable to a preselected pressure.

* * * * *